(12) United States Patent
Lee

(10) Patent No.: US 7,639,151 B2
(45) Date of Patent: Dec. 29, 2009

(54) LIQUID BLOCKING APPARATUS AND SYSTEM EQUIPPED WITH AN ALARM OR WIRELESS CALLING DEVICE AND A STORING BAG

(76) Inventor: Sang-dae Lee, 5un-kyeong Apt 2 Dong-301Ho, 506, Daechi-dong, Kangnam-ku, Seoul (KR) 135-280

( * ) Notice: Subject to any disclaimer, the term of this patent is extended or adjusted under 35 U.S.C. 154(b) by 335 days.

(21) Appl. No.: 11/816,107

(22) PCT Filed: Feb. 9, 2006

(86) PCT No.: PCT/KR2006/000476

§ 371 (c)(1),
(2), (4) Date: Aug. 13, 2007

(87) PCT Pub. No.: WO2006/098551

PCT Pub. Date: Sep. 21, 2006

(65) Prior Publication Data

US 2009/0121885 A1   May 14, 2009

(30) Foreign Application Priority Data

Feb. 14, 2005  (KR) .................. 10-2005-0012000
Mar. 9, 2005   (KR) .................. 10-2005-0019760

(51) Int. Cl.
 *G08B 21/00* (2006.01)
 *F16K 15/00* (2006.01)
 *F16K 17/00* (2006.01)
 *A61M 5/00* (2006.01)
(52) U.S. Cl. ............... 340/608; 340/603; 340/606; 340/609; 137/517; 137/518; 137/521; 137/601.21; 137/602; 604/245; 604/246; 604/247; 604/248; 604/249; 604/251; 604/256; 604/257; 604/264
(58) Field of Classification Search ......... 340/603–608; 137/517–521, 601.21, 602; 604/245–257, 604/264
See application file for complete search history.

(56) References Cited

U.S. PATENT DOCUMENTS 2,609,281 A * 9/1952 Smith ..................... 48/192

(Continued)

FOREIGN PATENT DOCUMENTS

JP       2002-287830 A    10/2002

(Continued)

*Primary Examiner*—Benjamin C Lee
*Assistant Examiner*—Lam P Pham
(74) *Attorney, Agent, or Firm*—Birch, Stewart, Kolasch & Birch, LLP

(57) ABSTRACT

The present invention is related to a liquid blocking apparatus and a system thereof, wherein if the liquid contained in an IV bag or a liquid tank is oozed out completely, the flow of liquid is blocked, the alarm lamp is turned on, the alarm sound is generated, and then the supply of liquid is maintained for a predetermined time. A liquid blocking apparatus, or an IV set according to the present invention comprises an elastic support strip having a concave portion in a center thereof; an elastic operation strip having a convex portion in contact with said concave portion of said elastic support strip; and a housing including an inlet through which liquid is introduced, and an outlet from which liquid flows out are arranged at an upper and lower side thereof, wherein a pair of an elastic support strip and an elastic operation strip are mounted on one side thereof, and an alarm or a wireless calling device that transmits a wireless signal to the receiver of the integrated briefing room is mounted on the other side thereof, and a storage bag just below the housing. If the liquid is introduced, the convex portion of said elastic operation strip which is in contact with the concave portion of said elastic support strip is projected toward an opposing direction due to the water pressure, and the liquid can pass by, and if the liquid is not introduced, the convex portion of said elastic operation strip covers and blocks the outlet of said housing due to the force for restoring to an original form, and the liquid stored in the storage bag is supplied continuously for a predetermined time.

5 Claims, 5 Drawing Sheets

| U.S. PATENT DOCUMENTS | | | | | FOREIGN PATENT DOCUMENTS | | |
|---|---|---|---|---|---|---|---|
| 5,623,465 | A * | 4/1997 | Sasaki et al. ............. 369/44.32 | KR | 1990-15764 | A | 11/1990 |
| 7,527,241 | B2 * | 5/2009 | Lodolo ...................... 251/331 | KR | 1999-19250 | A | 3/1999 |
| 2004/0084089 | A1 | 5/2004 | Yamashita | KR | 2001-61103 | A | 7/2001 |
| 2004/0102738 | A1 * | 5/2004 | Dikeman et al. ............ 604/256 | WO | WO-03-45475 | A | 6/2003 |
| 2005/0065480 | A1 | 3/2005 | Lee et al. | | | | |

* cited by examiner

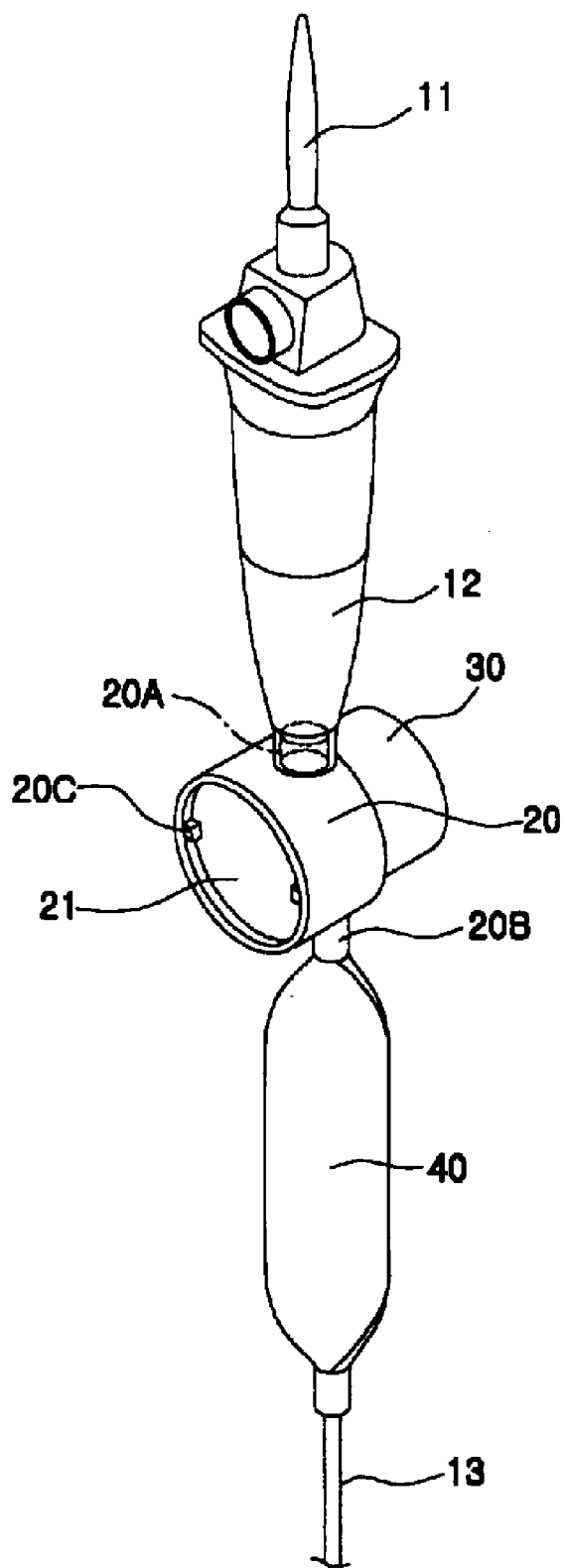
[Fig. 1]

[Fig. 2]
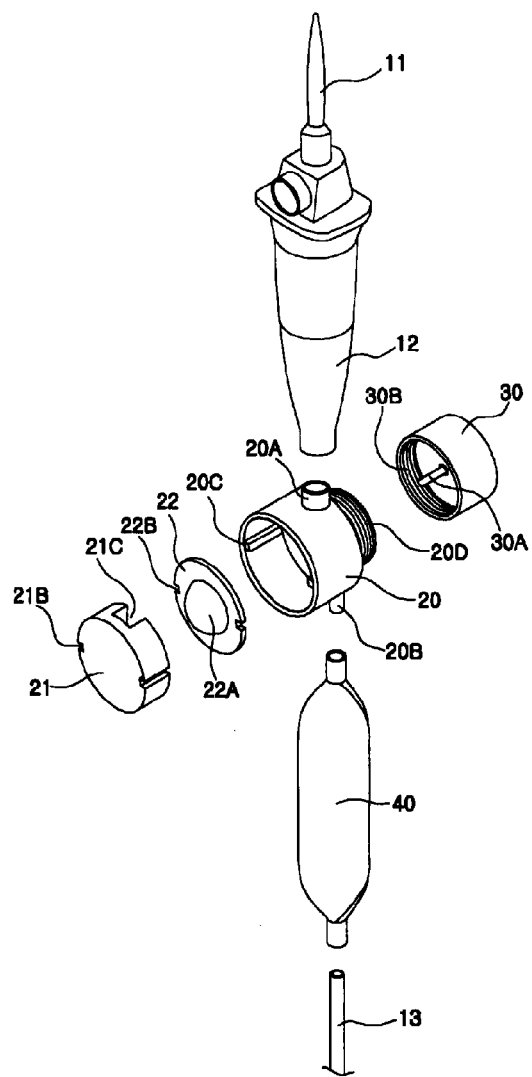
[Fig. 3]
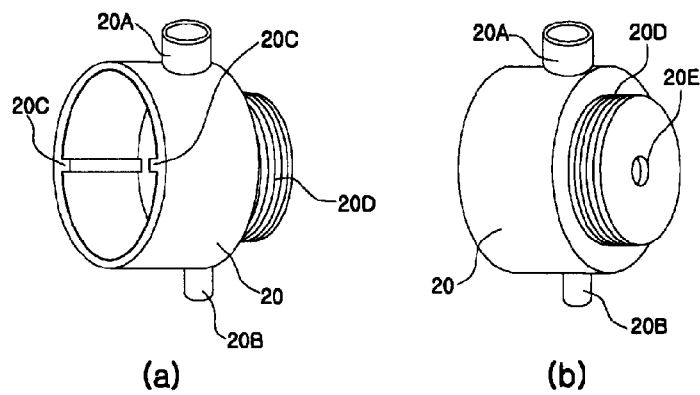

[Fig. 4]
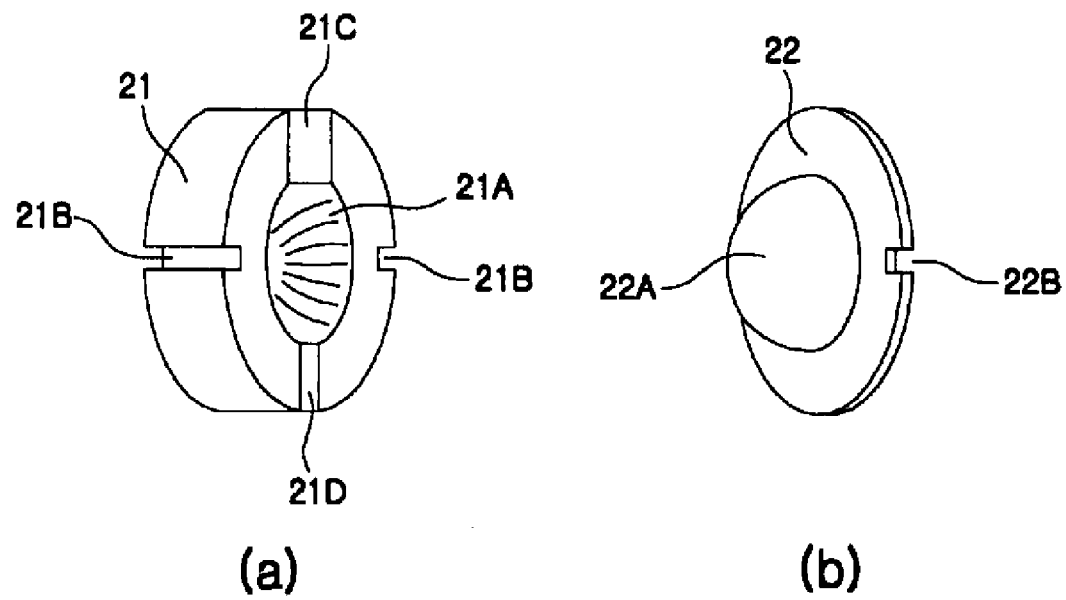
(a)  (b)
[Fig. 5]
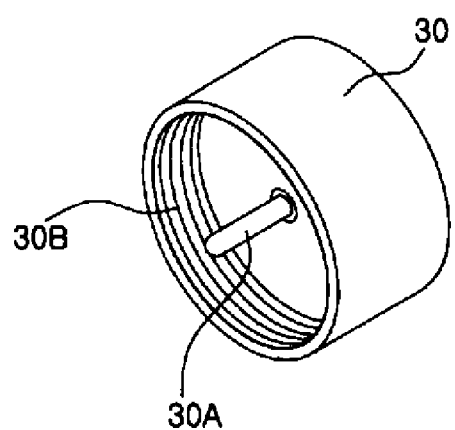

[Fig. 6]
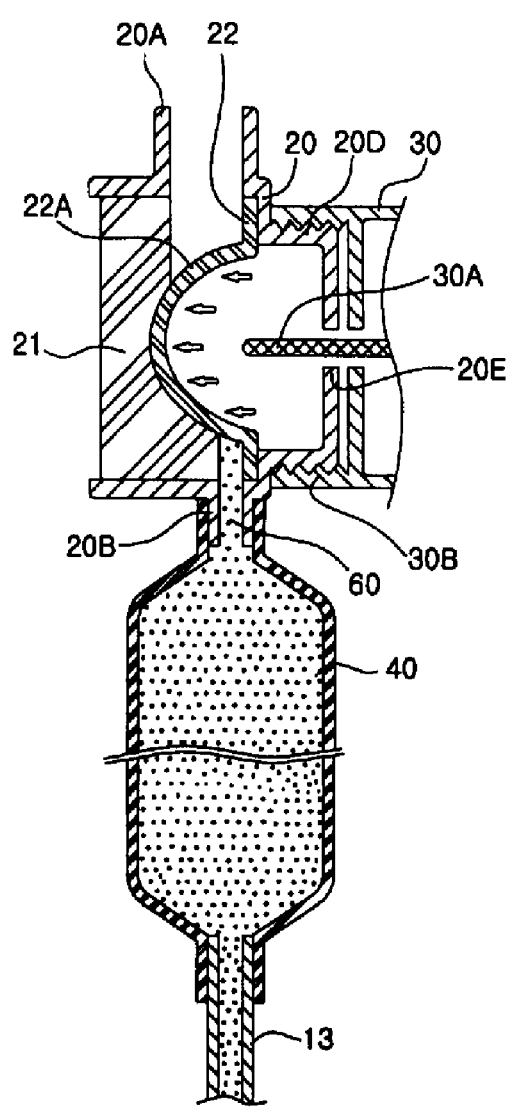
(a)
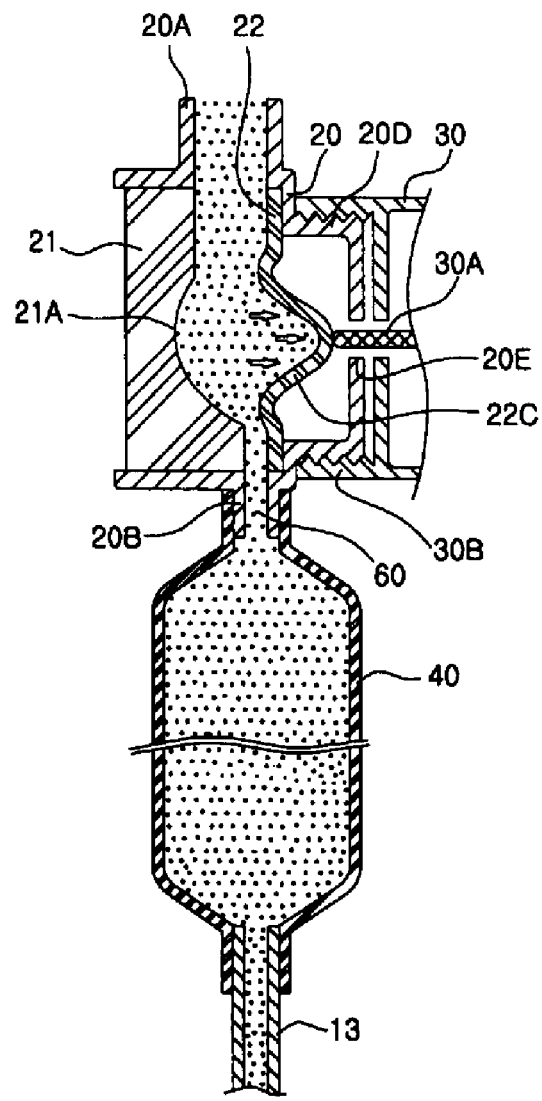
(b)

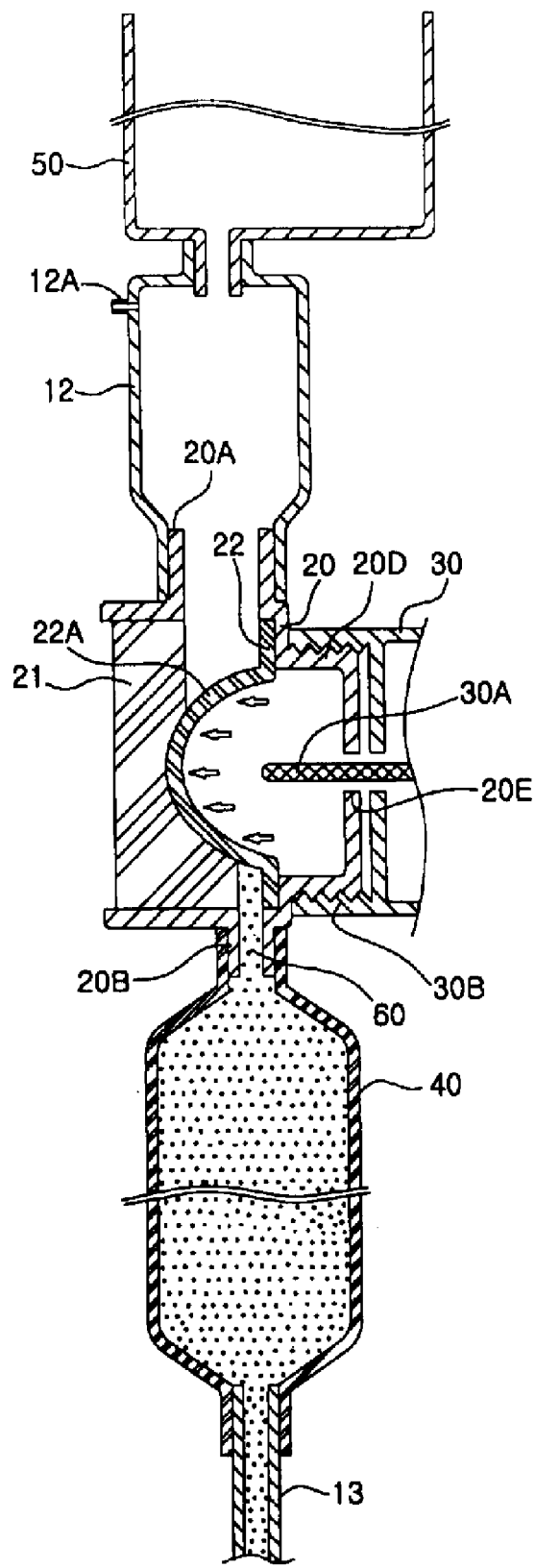
[Fig. 7]

LIQUID BLOCKING APPARATUS AND SYSTEM EQUIPPED WITH AN ALARM OR WIRELESS CALLING DEVICE AND A STORING BAG

TECHNICAL FIELD

The present invention is related to a liquid blocking apparatus and a system thereof, wherein if the liquid contained in an IV(intravenous) bag or a liquid tank is oozed out completely, the flow of liquid is blocked, the alarm lamp is turned on, the alarm sound is generated, and then the supply of liquid is maintained for a predetermined time.

BACKGROUND ART

In the prior art, when an IV bag is injected into the patients, even if the IV fluid is injected completely into the patients, there were cases that the protectors or the patients could not recognize the state, and thus the blood of the patients flows reversely. Therefore, there was a problem that the patients or the protectors should always watch the injection state with very keen attention even during the injection of the IV fluid because they could not know exactly the time when the injection of the IV fluid is completed.

Accordingly, an invention was developed in which a small round ball is inserted into a drip chamber of an IV set, and if the IV fluid is injected completely, the round ball blocks the outlet of the IV set, and thus prevents the patients' blood from flowing reversely.

But, such a conventional invention could not solve the problem that when the IV fluid is injected completely, the round ball can not block the outlet of the IV set surely, and thus the patients or the protectors are not satisfied.

DISCLOSURE OF INVENTION

Technical Problem

The present invention is disclosed to solve above-mentioned problem, and the object of the present invention is to provide a liquid blocking apparatus and a system thereof, wherein if the liquid is injected into the patients completely, the outlet is blocked swiftly and accurately, the alarm lamp is turned on, the alarm sound is generated for notifying the completion of the injection, and then the supply of liquid is maintained for a predetermined time.

Technical Solution

In an IV set wherein an IV set having a liquid blocking function according to the present invention is connected to an IV bag for injecting the IV fluid, said IV set comprises an elastic support strip having a concave portion in a center thereof; an elastic operation strip having a convex portion in contact with said concave portion of said elastic support strip; and a housing including an inlet through which IV fluid is introduced, and an outlet from which IV fluid flows out are arranged at an upper and lower side thereof, wherein a pair of an elastic support strip and an elastic operation strip are mounted on one side thereof, and wherein said convex portion of said elastic operation strip in contact with said concave portion of said elastic support strip is projected toward the opposing direction of said concave portion due to water pressure when IV fluid is introduced, and then IV fluid passes by, and said convex portion of said elastic operation strip becomes in close touch with said elastic support strip by a force for restoring to an original form when IV fluid is not introduced, thereby the outlet of said housing is covered and blocked.

Advantageous Effects

If the liquid is introduced, the convex portion of said elastic operation strip which are in contact with the concave portion of said elastic support strip is projected toward an opposing direction due to the water pressure, and the liquid can pass by, and if the liquid is not introduced, the convex portion of said elastic operation strip becomes in close touch with said concave portion of said elastic support strip by a force for restoring to an original form, thereby the outlet of said housing is covered and blocked and then liquid of an IV tube does not flow out, and the liquid stored in the storage bag is supplied continuously for a predetermined time.

BRIEF DESCRIPTION OF THE DRAWINGS

FIG. 1 is a view showing an IV set to which a liquid blocking apparatus according to the present invention is applied.

FIG. 2 is a view analytically showing the IV set of FIG. 1.

FIG. 3a is a view showing a housing of FIG. 2 and FIG. 3b is a view showing the opposing side of the housing of FIG. 2.

FIG. 4a is a view showing the elastic support strip of FIG. 2 and FIG. 4b is a view showing the elastic operation strip of FIG. 2.

FIG. 5 is a view showing an alarm or a wireless calling device of FIG. 2.

FIG. 6a is a cross-sectional view showing a blocking state of the IV set of FIG. 2, and FIG. 6b is a view showing a passage state of the IV set of FIG. 2.

FIG. 7 is a cross-sectional view showing a blocking state of a liquid tank to which a liquid blocking apparatus according to the present invention is applied.

BEST MODE FOR CARRYING OUT THE INVENTION

Furthermore, It is preferable that an IV set according to the present invention includes an alarm button, and further comprises an alarm or a wireless calling device wherein when the alarm button is projected, an alarm lamp is turned on and an alarm sound is generated, and when the alarm button is pressed, an alarm lamp is not turned on and an alarm sound is not generated.

Preferably, an alarm button opening formed on the other side of said housing for mounting or detaching the alarm or the wireless calling device by rotation is provided in a center thereof through which an alarm button can be inserted. When liquid is introduced, the alarm button is pressed since the convex portion of said elastic operation strip is projected toward an opposing direction so that an alarm lamp is not turned on and an alarm sound is not generated. When liquid is not introduced, the alarm button is projected to an original position since the convex portion of said elastic operation strip is restored to the original position so that the alarm lamp is turned on and the alarm sound is generated.

On the other hand, it is preferable that an IV set according to the present invention further comprises a storage bag which is arranged just below said housing for holding the liquid so that it can be supplied for a predetermined time even though the liquid is not introduced from the IV bag.

The storage bag is formed with a vinyl material, and when the liquid is introduced, the bag is bloated and when the liquid is not introduced, the bag is shrinked.

MODE FOR THE INVENTION

Next, the embodiment of the present invention will be explained in detail with referring to the drawings.

FIG. 1 is a view showing an IV set to which a liquid blocking apparatus according to the present invention is applied.

As described in FIG. 1, the IV set includes a spike 11, a drip chamber 12, a housing 20, a storage bag 40, an IV tube 13 for guiding the IV fluid, and an alarm or a wireless calling device 30.

FIG. 2 is a view analytically showing the IV set of FIG. 1.

The drip chamber 12, and the storage bag 40 are inserted into an inlet 20A, and an outlet 20B which are formed at the upper and lower portion of the housing 20 of the IV set, respectively. The IV tube 13 is arranged below the storage bag 40.

A pair of an elastic support strip 21 and an elastic operation strip 22 are inserted into one side of the housing 20 of the liquid blocking apparatus for allowing the IV fluid to flow or to be blocked by detaching or attaching.

Besides, an alarm or a wireless calling device 30 which generates an alarm sound and turns on an alarm lamp when the IV fluid is oozed out completely from an IV bag is inserted into the other side of the housing 20 of the liquid blocking apparatus.

FIG. 3a is a view showing a housing of FIG. 2 and FIG. 3b is a view showing the opposing side of the housing of FIG. 2.

A pair of an elastic support strip 21 and an elastic operation strip 22 are inserted into one side of the housing 20 of an open cylindrical shape. A plurality of projections 20C which are in contact with the projection grooves 21B, 22B of an elastic support strip 21 and an elastic operation strip 22 when an elastic support strip 21 and an elastic operation strip 22 are inserted are formed.

On the other hand, a screw thread connection unit 20D of an open cylindrical shape is formed on the other side of the housing 20 for mounting or removing an alarm or a wireless calling device 30 which generates an alarm sound and turns on an alarm lamp when the IV fluid is oozed out completely from an IV bag. An alarm button opening 20E into which an alarm button 30A can be inserted is formed in a center of this screw thread connection unit 20D.

Furthermore, the screw thread connection unit 20D includes a screw thread in an exterior wall for screwing up an alarm or a wireless calling device 30.

FIG. 4a is a view showing the elastic support strip of FIG. 2 and FIG. 4b is a view showing the elastic operation strip of FIG. 2.

An elastic support strip 21 having a concave portion 21A in the center thereof is in contact with an elastic operation strip 22 having a convex portion 22A in the center thereof, and a plurality of projection grooves 21B, 22B are formed such that they are engaged with a plurality of projections 20C formed in the housing 20. Therefore, when an elastic support strip 21 and an elastic operation strip 22 are inserted into the housing 20, they are not removed or swayed. An elastic support strip 21 includes an inlet groove 21C which is connected to the inlet 20A in the upper portion, and an outlet groove 21D which is connected to the outlet 20B in the lower portion. It is preferable that the inlet 20A and the inlet groove 21C are formed to be large for enabling the air to be flowed smoothly to the drip chamber 12. An elastic support strip 21 and an elastic operation strip 22 are formed with elastic latex or silicon having very excellent restoring force, and the convex portion 22A of an elastic operation strip 22 is made to be thin so that it may be projected toward the opposing direction due to a very small water pressure of the IV fluid.

FIG. 5 is a view showing an alarm or a wireless calling device of FIG. 2.

As described in FIG. 5, an alarm button 30A is projected in the center of one side of an alarm or a wireless calling device 30. This alarm button 30A is inserted into an alarm button opening 20E of the housing 20.

Usually, that is, when the IV fluid is flowing normally, the alarm button 30A is pressed by the elastic operation strip 22, and in case of an emergency, that is when the IV fluid is oozed out completely, the alarm button 30A is separated from the elastic operation strip 22.

Furthermore, a screw groove connection unit 30B is formed in an alarm or a wireless calling device 30, and a screw groove is formed such that it may be screw-connected to the screw thread connection unit 20D of the housing 20 in the screw groove connection unit 30B.

Therefore, when the users mount an alarm or a wireless calling device 30 on the IV set, they can mount it by screwing up, and at this time, the screw thread connection unit 20D of the housing 20, and the screw groove connection unit 30B of an alarm or a wireless calling device 30 are connected.

When the alarm button 30A is pressed, an alarm or a wireless calling device 30 does not generate an alarm sound and does not turn on the alarm lamp. When the alarm button 30A is projected due to the operations of the devices such as a spring mounted on an alarm or a wireless calling device 30, alarm sound is generated and the alarm lamp is turned on. In addition, when an alarm or a wireless calling device 30 is not used, they are put in upside-down state. Then the alarm button 30A is in a pressed state, and thus alarm sound is not generated and the alarm lamp is not turned on. An alarm or a wireless calling device 30 using the alarm button 30A is one example of the present invention, and various kinds of an alarm or a wireless calling device 30 on which a sensor for sensing the movement of the convex potion 22A of an elastic operation strip 22 is mounted can be manufactured.

A small wireless calling device 30 transmits a signal wirelessly to the receiver of a nurse station by the operation of the alarm button 30A.

On a screen display unit of the receiver of a nurse station, a red alarm lamp is turned on in the position of the patient into whom the IV fluid is injected completely, and an alarm sound is generated to notify that the IV fluid of the IV bag is injected completely into the patient. Therefore, it is possible for a nurse to replace the vacant IV bag with a new one immediately after grasping synthetically the patient into whom the IV fluid is injected completely without the observation of the patient's protectors. Furthermore, when a new IV bag is exchanged, a signal is transmitted wirelessly to the receiver of a nurse station. Then, the red alarm lamp which is being turned on, and the alarm sound which is being generated on the screen display unit for monitoring all patients are stopped.

An alarm or a wireless calling device 30 can be formed by a melody generation circuit, or a wireless calling circuit including a small battery, a red alarm lamp, and general IC circuit. The device and the structure of the alarm is same to those embedded in the melody card, and the structure of the wireless calling device is same to that of a wireless calling button arranged in the tables of the restaurants.

Next, the operations of the IV set according to the present invention will be explained with referring to FIG. 6.

If the IV fluid 60 starts to be introduced through the inlet 20A from the IV bag, and a predetermined amount of IV fluid 60 is stored into the housing 20, the convex portion 22A of an elastic operation strip 22 which is engaged with the concave portion 21A of an elastic support strip 21 is projected toward the opposing direction due to the water pressure as shown in FIG. 6b. At this time, the alarm button 30A is pressed by the reverse convex portion 22C of an elastic operation strip 22, and thus an alarm sound is not generated and an alarm lamp is not turned on.

But, if the IV fluid 60 is not introduced through the inlet 20A from the IV bag anymore, the convex portion 22A of an elastic operation strip 22 becomes in a close touch with anelastic support strip 21, covers and blocks the outlet 20B of the housing 20. Accordingly, the IV fluid 60 existing below the outlet 20B does not flow downwardly anymore, and thus the blood of a patient does not flow reversely. In addition, the convex portion 22A of an elastic operation strip 22 is restored to an original form, and the pressed alarm button 30A is returned to the original position so that an alarm sound is generated and an alarm lamp is turned on.

At this time, even though there is no IV fluid 60 introduced from the IV bag, since the IV fluid 60 stored in the storage bag 40 starts to flow down through the IV tube 13, the IV fluid 60 can be administered continuously to the patient without let-up.

Therefore, a nurse can exchange the old IV bag with a new one, or pull out the needle inserted into the body of the patients comfortably. The storage bag 40 can be made to be larger to give a nurse more time to replace the old IV bag with a new one.

FIG. 7 is a cross-sectional view showing a blocking state of a liquid tank to which a liquid blocking apparatus according to the present invention is applied.

As is shown in FIG. 7, in a liquid tank to which a liquid blocking apparatus according to the present invention is applied, the liquid blocking apparatus is operated based upon those which are same to the principles of said IV set, and comprises an air discharge pipe 12A, a drip chamber 12, a housing 20 including the elastic operation strip 22 and the elastic support strip 21, a storage bag 40, a supply tube 13, and an alarm or a wireless calling device 30.

Since the drip chamber 12 is provided with an air discharge pipe 12A, it is possible to adjust the water level suitably in the drip chamber 12 by discharging the air of the drip chamber 12.

After comparing with FIG. 1, same reference symbols are given to same parts, and the detail explanation will be omitted.

As is described above, in a liquid blocking apparatus of a liquid tank to which the liquid blocking apparatus according to the present invention is applied, if the liquid 60 is not introduced anymore through the inlet 20A from the liquid tank 50, the convex portion 22A of an elastic operation strip 22 becomes in a close touch with the concave portion 21A of an elastic support strip 21, covers and blocks the outlet 20B of the housing 20. Accordingly, since the convex portion 22A of an elastic operation strip 22 does not press the alarm button 30A anymore, an alarm sound is generated and an alarm lamp is turned on.

In addition, even though there is no liquid introduced from the liquid tank 50, the liquid 60 stored in the storage bag 40 is supplied continuously through the supply tube 13 for a constant time. Therefore, the manager of the liquid tank can fill the liquid tank with the liquid comfortably.

An oil tank of a boiler can be enumerated as an example of such a liquid tank.

INDUSTRIAL APPLICABILITY

According to the liquid blocking apparatus of the present invention, if the liquid is injected completely from the liquid tank or an IV bag, they are blocked and an alarm lamp is turned on, and an alarm sound is generated by an alarm or a wireless calling device. Then, the liquid is supplied continuously for a constant time.

Therefore, in case of the IV set, it is not necessary to confirm the remaining amount of the IV fluid frequently, and it is also possible to replace the old IV bag with the new one immediately before the blood vessels are blocked. Furthermore, when the IV fluid in the IV set is injected completely, the blood can be prevented from flowing reversely into the IV set. Besides, since the storage bag is arranged, it is possible to exchange an IV bag comfortably under the state that the IV fluid is being injected.

In case of a liquid tank, the air is blocked not to be introduced into the supply tube, and the supply amount can be adjusted minutely by confirming the falling drops, or the present used amount in a real time can be confirmed in the naked eye. After an alarm lamp is turned on and an alarm sound is generated by an alarm or an wireless calling device at the same time of blocking, the liquid is suppled continuously for a constant time by the storage bag until the liquid is filled up in the liquid tank.

Since the wireless calling device sends a signal wirelessly to the receiver of the integrated briefing room, the overall management of solution tanks of hundreds of solutions which are produced for the industrial applications as well as the overall management of hundreds of the IV bags becomes possible.

As mentioned above, the preferred embodiment of the present invention is described and illustrated, but the present invention is not limited to the above-mentioned specific embodiment, and it is natural that various changes and modifications can be made by the person in the art to which the present invention pertains without departing the scope of gist of the present invention claimed in the claims. Those changes and modifications are described within the scope of the claims.

The invention claimed is:

1. A liquid blocking apparatus connected to a liquid tank or an IV bag for injecting liquid comprising,
   an elastic support strip having a concave portion in a center thereof;
   an elastic operation strip having a convex portion in contact with said concave portion of said elastic support strip; and
   a housing including an inlet through which liquid is introduced, and an outlet from which liquid flows out and arranged at an upper and lower end thereof,
   wherein a pair of said elastic support strip and said elastic operation strip are mounted on one side thereof, wherein said convex portion of said elastic operation ship attached to said concave portion of said elastic support strip is protruded toward the opposing direction of said concave portion due to liquid pressure when liquid is introduced, and then liquid starts to flow, and said convex portion of said elastic operation strip becomes in close touch with said elastic support strip by convex portion closing force for restoring to an original form when liquid is not introduced, thereby the outlet of said housing is covered and blocked, and then liquid of an IV tube does not flow out;
   a screw thread connection unit which is formed on the other side of said housing for attaching and detaching an alarm or a wireless calling device, and includes an alarm button opening formed in a center thereof through which an alarm button can be inserted, said alarm button is pressed when the convex portion of said elastic operation strip is projected toward an opposing direction when liquid is introduced, so that an alarm lamp is not turned on and an alarm sound is not generated, and said alarm button is projected to an original position when the convex portion of said elastic operation strip is restored to the original position when liquid is not introduced, so that the alarm lamp is turn on and the alarm sound is generated.

2. A liquid blocking apparatus set forth in the claim 1, wherein said alarm includes said alarm lamp and said alarm sound.

3. A liquid blocking apparatus set forth in the claim 1, wherein, said wireless calling device is designed such that when said alarm button is pressed, then a first wireless calling signal indicating the introduction of the liquid is transmitted, and then a second wireless calling signal indicating that the liquid is not introduced is transmitted when said alarm button is projected to the original position.

4. A liquid blocking device set forth in the claim 1, further comprising a storage bag which is formed with a vinyl, and is arranged just below said housing for holding the liquid so that it can be supplied for a predetermined time even though the liquid is not introduced from the IV bag or the liquid tank.

5. A liquid blocking system having a liquid blocking apparatus, and a receiver of an integrated briefing room, said liquid blocking apparatus comprising, an elastic support strip having a concave portion in a center thereof;

an elastic operation strip having a convex portion in contact with said concave portion of said elastic support strip;

a housing including an inlet through which liquid is introduced, and an outlet from which liquid flows out me arranged at an upper and lower end thereof, wherein a pair of said elastic support strip and said elastic operation strip are mounted on one side thereof; and a screw thread connection unit which is formed on the other side of said housing for attaching and detaching a wireless calling device, and includes an alarm button opening formed in a center thereof through which an alarm button can be inserted, wherein the wireless calling device is designed such that when said alarm button is pressed and then a first wireless calling signal indicating the introduction of the liquid is transmitted when the convex portion of said elastic operation strip is projected toward an opposing direction when liquid is introduced, so that an alarm lamp is not turned on and an alarm sound is not generated, and said alarm button is projected to an original position when the convex portion of said elastic operation strip is restored to the original position when liquid is not introduced, and then a second wireless calling signal indicating that the liquid is not introduced is transmitted, so that the alarm lamp is turned on and the alarm sound is generated, said receiver of the integrated briefing room comprising, a receiving device arranged remotely from said wireless calling device for receiving a wireless calling signal generated from said wireless calling device; and a screen display unit for displaying a position and a state of said wireless calling device, wherein if said second wireless calling signal is received, the alarm lamp is turned on and the alarm sound is generated in a corresponding wireless calling device position of said screen display unit, and if said first wireless calling signal is received, the alarm lamp is not turned on and the alarm sound is not generated in said corresponding wireless calling device position of said screen display unit.

* * * * *